United States Patent [19]

Cherqui et al.

[11] 4,229,428
[45] Oct. 21, 1980

[54] GALENICAL FORM OF ADMINISTRATION OF BETAHISTINE AND ITS DERIVATIVES

[76] Inventors: Jean S. Cherqui, 55, Rue Pergolèse, 75016 Paris; Alain C. Djiane, 105, Avenue du Roule, 92200 Neuilly sur Seine, both of France

[21] Appl. No.: 27,351

[22] Filed: Apr. 5, 1979

[51] Int. Cl.² .......................... A61K 9/22; A61K 9/32
[52] U.S. Cl. ........................................ 424/19; 424/21; 424/32; 424/33; 424/35; 424/81
[58] Field of Search ................... 424/19–22, 424/32, 35, 81

[56] References Cited

U.S. PATENT DOCUMENTS

| | | | |
|---|---|---|---|
| 3,247,066 | 4/1966 | Milosovich | 424/35 X |
| 3,538,214 | 11/1970 | Polli et al. | 424/19 |
| 3,775,537 | 11/1973 | Lehmann et al. | 424/21 |
| 3,835,221 | 9/1974 | Fulberth et al. | 424/20 |
| 3,954,959 | 5/1976 | Pedersen | 424/21 |
| 4,083,949 | 4/1978 | Benedikt | 424/19 |

FOREIGN PATENT DOCUMENTS 2035301  2/1971  Fed. Rep. of Germany.

OTHER PUBLICATIONS

Merck Index 9th Ed (1976), Merck & Co., Rahway, N.J., p. 1208, #1206, "Betahistine" (HCL Vasodilator).
Fossel Chem. Abstr. 75, #25394t (1971) of Ger. Off. 2,035,301, Feb. 18, 1971.
Konzett et al., Chem. Abstr. 75 #62007q (1971) of J. Pharmacol. Exp. Thor. 1971 178(1).
Palazzoadriano et al., Chem. Abstr. 79 #28512n (1973) of Boll. Soc. Ital. Cardiol (1970) 15(s): 388–401.

*Primary Examiner*—Shep K. Rose

[57] ABSTRACT

There is provided a medicament in a form having surprising effectiveness against vertigo in Meniere's syndrome. This medicament comprises, as active ingredient, betahistinemethanesulfonate. The medicament further comprises a core of pharmaceutially acceptable thereapeutically inert carrier material having the active ingredient absorbed thereon, said active ingredient being covered with a dialysis membrane said membrane further carrying a second layer of active ingredient which, if desired, is itself absorbed upon a layer of therapeutically inert carrier material and is covered with a further dialysis membrane. There may be utilized a plurality of substantially concentric layers of active material suitably absorbed on the carrier, and covered with a dialysis membrane to provide a long-acting medicament form.

6 Claims, No Drawings

GALENICAL FORM OF ADMINISTRATION OF BETAHISTINE AND ITS DERIVATIVES

The object of the present invention is to treat the buzzing of the ears and the vertigo of Meniere's syndrome with this new pharmaceutical product.

It is known that this type of symptom appears mostly in the elderly patient, that long term treatment is necessary and that perfect tolerance of the product is therefore required.

Until now, the principal product used in the treatment of these problems is 2-methylaminoethyl pyridine hydrochloride, also called betahistine hydrochloride. However, this product, although very valuable therapeutically, has had limited success on the market because of the precautions necessary during its usage and because of the side effects occuring during treatment. Also, the short action of this substance necessitates frequent doses. In fact, the daily dosage can be as much as 48 mg, taken in 6 dividided doses.

It is known that betahistine has a histamine-like action on the secretion cells of the gastric mucosa and that its use is inadvisable in patients with gastric ulcers, or suffering from gastric hyperchlorhydria.

It was thus advantageous to be able to have at our disposal a new pharmaceutical form which assures regular and prolonged diffusion of the active ingredient while eliminating the risks of intolerance.

The pharmaceutical forms according to the invention avoid the previously mentioned inconveniences and place at the disposal of the doctor a new therapeutic agent which has a safety level and weak enough dose to allow long term treatment.

The pharmaceutical forms according to the invention are characterised by the presence of betahistine methane sulphonate contained in microcapsules which are in turn contained in small spheres with semi-permeable membranes. This pharmaceutical form releases betahistine progressively as the pH of the digestive juices increases.

According to the invention the semi-permeable membrane consists of successive concentric largers of metacrylic polymers and the thickness of the membrane determines the rate of release of the active ingredient. The active ingredient is incorporated in these microgranules in the form of a dispersion in an inert substance and is dispersed in themetacrylic mass or solutions of this polymer in a volatile solvent.

To cite examples, the inert substance can be starch, talc, lactose, saccharose, colloidal silica, celluloses, magnesium stearate, magnesium phosphate or alumina.

The metacrylic polymer is preferably that sold under the brand name of Eudragit, registered trademark of Rohm Pharma GmbH, Darmstadt, Federal Republic of Germany.

The pharmaceutical forms according to the invention are presented in the form of transparent or opaque capsules containing a fixed number of microgranules or powders, in the form of flavoured or unflavoured suspensions.

On contact with the digestive juices in the stomach, the capsules open and release a large number of these microgranules which thus converts one dose into a large number of autonomic sub-doses. This multiplication allows a greater dispersion and thus a satisfactory absorption and a prolonged action.

The capsules according to the invention contain 10 to 15 mg, and preferably 12 mg, of the active ingredient.

The daily dose is 2 to 3 capsules, preferably 3. It can thus be seen that the composition of the invention allows treatment of the vertigo of the type caused by Meniere's disease with a dose which is reduced by 50% and prevents, to the highest possible degree, undesirable side effects. The duration of treatment is from 6 weeks to 6 months according to the therapeutic indications.

The compositions according to the invention were tested in the treatment of the vertigo of Meniere's disease and in the treatment of cerebral circulatory insufficiency. These treatments are particularly intended for the elderly patient (70 or over) but younger patients were nevertheless treated under identical conditions.

Example of the manufacture of a pharmaceutical form according to the invention

A starting granule of a mixture of starch, saccharose and stearic acid is made. The sifted granules are placed in a turbine which has sufficient speed and rotating time to obtain perfectly spherical grains. A second sieving is carried out, then the granules are dried.

A certain quantity granules is wetted with ethanol, then is coated with betahistine methane sulphonate solution again using a turbine. Talc and stearic acid are added to facilitate coating. The granules are then dried in a ventilated dryer.

This operation is performed several times.

Once finished a solution of metacrylic polymers is powdered for coating. The microgranules thus obtained are dried for 2 to 4 days in a ventilated dryer.

In the next step, the determination of the active microgranules is carried out, and the necessary quantity of inactive non-coated microgranules is added until a mixture containing 12 mg of betahistine per 240 mg of microgranules is obtained. The microgranules are then placed in capsules, each capsule containing 240 mg of microgranules.

Example of manufacture of 100,000 capsules

| | |
|---|---|
| active microgranules | |
| Betahistine methanesulphonate | 1.200 kg |
| Eudragit, registered trademark of Rohm Pharma GmbH, Darmstadt, Federal Republic of Germany | |
| stearic acid, talc | |
| saccharose, corn starch, aerosil | 20.800 Kg |
| inactive microgranules | |
| saccharose, corn starch, stearic acid. | 2.000 Kg |
| | 24.000 Kg |

Additives in the manufacturing process:
Distilled water, 95% ethanol, acetone.

Assay of the rate of release of betahistine methanesulphonate

The rate of release of betahistine dimethanesulphonate is within the following limits:
1st hour: less than 40% released
4th hour: less than 80%
8th hour more than 80%

These controls were carried out in controlled conditions, using the appropriate equipment, to reproduce conditions encountered in the body.

Thus the liberation during the first hour is tested in artificial gastric medium with pH 1.5 and after 1 hour the medium is changed and the microgranules are placed in artificial intestinal medium at pH of 7.2.

The equipment used allows constant stirring and a constant temperature of between 36.5° C. and 37.5° C.

Each manufacturing batch of microgranules can be thus tested and the coating modified accordingly.

REPORT OF CLINICAL TRIALS

A-Cerebral circulatory insufficiency problems

The clinical trials were conducted in 40 patients The trial was double blind with a placebo as reference product.

The duration of treatment was 12 weeks, divided in two periods of 6 weeks with a 2 weeks wash-out period in between. The wash-out period was necessary to ensure that there were no remaining effects from the preceding treatment.

The order of administration of the treatments was determined at random and the code provided by the manufacturer was kept in a sealed envelope, to be opened only at the completion of the trial.

The distribution of the medication and their administration was regulated using a standard protocol, throughout the duration of the trial. The standardisation of the nursing, to which we attached great importance in the evolution of a therapy destined to improve the cerebral circulation in senescent patients, was rigorously observed.

The psychometric tests designed to evaluate the CRICHTON rating scale were performed in the same department, following particularly throughly tested methods.

Results

The results were evaluated from both the clinical and psychological points of view. This evaluation was facilitated by the use of the Crichton rating scale. The systematic study of the different parameters permitted accurate evaluation of the items improved after each treatment.

We classed the results as: Good, Medium Failure, being based on both the clinical state of the patient and on the number of items improved.

GOOD

The whole group of items improved

MEDIUM

An improvement, indicated by the different parameters, from subjective and objective points of view.

FAILURE

Persistent debility (physical and psychological) reflected in a lack of change in the tests, negative to begin with, and an unchanged clinical status.

(2°) Tolerance (a) Biological telerance

We used the normal tests for verifying the tolerance, bearing in mind the known characteristics of betahistine. The following tests were performed before and after the treatments:
urea
glucose
cholesterol
transaminase SGOT/SGPT
haemoglobin
blood count (b) Clinical tolerance We considered cardiovascular surveillance to be of utmost importance. We performed the following tests:
arterial blood pressure before, during and after treatment.
cardiac rhythm before, during and after treatment
ECG before and after treatment Gastrointestinal surveillance, intestinal transit time, nausea, vomiting and neurological surveillance were performed by the nursing saft, as well as the observations followed in the tests for measuring the effectiveness of the product.

RESULTS

The treatment was divided into 2 periods of 6 weeks. The results obtained are as follows:

| 1st group: Series Placebo-Active product | | | |
|---|---|---|---|
| Placebo | 5 | medium results, | being 25% |
|  | 15 | failures | being 75% |
| Active product | 16 | good results, | being 80% |
|  | 3 | medium results, | being 15% |
|  | 1 | failure | being 5% |
| 2nd group: Series Active product-placebo | | | |
| Active product | 12 | good results, | being 60% |
|  | 4 | medium results, | being 20% |
|  | 4 | failures | being 20% |
| Placebo | 20 | failures | being 100% |

These results show a net improvement under treatment with the active product, being:
28 good results, being 70%
7 medium results, being 17,5%
5 failures, being 12,5%

ANALYSIS OF RESULTS 40 patients were treated in this controlled clinical trial which was double blind crossover with a placebo as reference product. The advantage of a trial of this nature is that only a limited number of subjects is necessary. There were:
11 male patients, representing 27,5% of the total
29 female patients, representing 72,5% of the total.

The number of patients corresponds to the number generally used in this type of trial.

Several remarks can be made at the end of this trial:
no patient stopped his treatment. during the trial
we observed no side effects.

The tolerance was in general good except for a few cases of mild intolerance.

The symptoms improved the most by treatment with the invention were:

| Series | placebo-active product: | |
|---|---|---|
|  | anxiety, fear | 77% |
|  | emotional stability | 73.7% |
|  | liveliness, confusion | 68.5% |
|  | reactional depression | 64.3% |
|  | vertigo | 61.5% |
|  | appetite | 61.5% |
|  | headaches | 54.55% |
|  | sleep | 53% |
|  | buzzing in the ears | 50% |
| Series | active product-placebo: | |
|  | axiety, fear | 86.7% |
|  | fatigue | 83.4% |
|  | emotional stability | 73.3% |
|  | liveliness, confusion | 69.2% |

| | |
|---|---|
| reactional depression | 62.5% |
| headaches | 62.5% |
| orientation | 57% |
| vertigo | 50% |

These results show that betahistine has, without any doubt, a positive effect on cerebral circulation. The results show in particular a marked improvement in the physiological status of the patients. The very significant improvement in certain items, such as vertigo, fatigue, headaches, sleep, buzzing in the ears, confirms the clinical effectiveness of the product in treating cerebral circulatory insufficiency.

(c) Biological tolerance

The biological tolerance was excellent in all cases. These were:
no modifications in blood count
no variations of urea, of glucose
no change in hepatic function.

(B) Treatment of Meniere's disease

The trial was conducted in 25 patients with an average age of 42,5 years. There were 10 men and 15 women. Patients selected were all patients presenting with a Meniere's syndrome of 6 months to 20 years since the onset.

The dosage and the therapeutic plan were established taking into account the level at which betahistine is active and at the same time the particular galenic form of the compositions according to the invention.

The betahistine was administered at a dosage level of 3 capsules per day, each capsule containing 12 mg of betahistine methanesulphonate.

The duration of treatment was fixed at least 3 months. This duration was extended to 6 or even 9 months in certain cases.

Criteria for evaluating effectiveness:

Meniere's disease in its acute phase is characterised by 3 definite symptoms:
vertigo
buzzing in the ears
deafness Vertigo is a symptom apart, in which the patient has the sensation that surrounding objects are moving in rotation.

The acute phase may last several hours and may be accompanied by spectacular neurovegetative signs.

The estimation of the clinical effectiveness of the product was based on such objective criteria. Before and after each treatment, labyrinthic tests, an audiogram were performed, then the following clinical signs were evaluated: vertigo, nausea, otalgia, headaches, tinnitus aurium.

Analysis of results

Independent of the clinical evaluation, it seemed necessary to divide the previously cited clinical parameters into: very good, good, quite good, medium, and failure.

At the same time, special importance was attached to gastrointestinal surveillance as well as to cardiovascular and neurological tolerance for the composition according to the invention.

Conclusions

At the end of the trial, it was seen that no patient interrupted treatment, and that there were no side effects and that the tolerance was overall very good for the compositions.

The trial was conducted in 25 patients, and the following results were obtained:

| | | | |
|---|---|---|---|
| very good and good results | = | 16 cases, being | 64% |
| quite good and medium | = | 6 cases, being | 24% |
| failure | = | 3 cases, being | 12% |

The results obtained thus show that the compositions according to the invention exert a very marked therapeutic activity and that the compositions are very active in the treatment of Meniere's syndrome and also that long term administration does not call for any particular caution.

Among the symptoms used as objective criteria, it is important to note that vertigo was improved in 88% of cases, nausea in 91% of cases and otalgia in all cases.

On the average, the delay of action of the product is 10 days; the duration of action lasts throughout treatment.

The pharmaceutical composition according to the invention were, from patient's remarks, much better tolerated than the non long-acting tablet form.

The biological tolerance was excellent in all cases.

We claim:

1. A therapeutically useful and pharmacologically acceptable oral depot medicament in the form of substantially uniformally sized spheroidal particles containing 2-methylaminoethyl pyridinemethanesulfonate as the active ingredient thereof comprising
    (a) an inactive core of pharmaceutically acceptable carrier material;
    (b) at least two sets of sequential bipartite layers on said core comprising an inner layer of the active ingredient and an outer layer of a dialysis membrane, said membrane being substantially insoluble in neutral or acid environments but soluble above pH 7.

2. A medicament in accordance with claim 1 wherein the inner layer of said sequential bipartite layer outwardly of the first dialysis membrane outwardly of the inactive core, additionally comprises pharmaceutically acceptable and pharmaceutically inert carrier material upon which the active ingredient is absorbed.

3. A medicament in accordance with claim 2 wherein said dialysis material is an anionic polimerizate of methacrylic acid and methacrylic esters.

4. A medicament in accordance with claim 3 wherein said medicament is further encapsulated in pharmaceutically acceptable capsules.

5. A method of treating vertigo in patients suffering from Meniere's syndrome which comprises administering to said patients an antivertigo effective amount of a composition of claim 1.

6. A method of claim 5 which comprises administering to said patients up to 48 mg per day of said active ingredient.

* * * * *